United States Patent
Snover et al.

(10) Patent No.: US 6,706,909 B1
(45) Date of Patent: Mar. 16, 2004

(54) RECYCLE OF DISCHARGED SODIUM BORATE FUEL

(75) Inventors: Jonathan Snover, Township of Jackson, Ocean County, NJ (US); Ying Wu, Borough of Red Bank, NJ (US)

(73) Assignees: Millennium Cell, Inc., Eatontown, NJ (US); US Borax, Valencia, CA (US)

( * ) Notice: Subject to any disclaimer, the term of this patent is extended or adjusted under 35 U.S.C. 154(b) by 0 days.

(21) Appl. No.: 10/435,771

(22) Filed: May 12, 2003

(51) Int. Cl.⁷ .................................................. C07F 5/04
(52) U.S. Cl. ........................................................ 558/296
(58) Field of Search .......................................... 558/296

(56) References Cited

U.S. PATENT DOCUMENTS

| | | |
|---|---|---|
| 2,534,533 A | 12/1950 | Schlesinger et al. |
| 2,884,440 A | 4/1959 | Tyson |
| 2,894,975 A | 7/1959 | Cunningham et al. |
| 2,938,920 A | 5/1960 | Cunningham et al. |
| 3,024,264 A | 3/1962 | Petterson |
| 3,210,157 A | 10/1965 | Lewis, Jr. et al. |
| 6,433,129 B1 | 8/2002 | Amendola et al. |
| 6,524,542 B2 | 2/2003 | Amendola et al. |

FOREIGN PATENT DOCUMENTS

CA 624125 7/1961

OTHER PUBLICATIONS

Maurice E. Indig and Richard N. Snyder, "Sodium Borohydride, An Interesting Anodic Fuel".
Journal of the Electrochemical Society, vol. 109, pp. 1104–1106, Nov. 1962.

*Primary Examiner*—Joseph K. McKane
*Assistant Examiner*—Robert Shiao
(74) *Attorney, Agent, or Firm*—Gibbons, Del Deo, Dolan, Griffinger, and Vecchione

(57) ABSTRACT

The present invention relates to an improvement in the recovery of boron values from a mixture of alkali metal borate and alkali metal hydroxide representing discharged fuel from a hydrogen generator apparatus. The mixture is reacted with carbon dioxide and a lower alcohol to form trialkyl borate, alkali bicarbonate and water. A porous water-absorbing material is added to the reaction mixture to absorb water as it forms thereby improving the yield of trialkyl borate. The trialkyl borate is converted to alkali borohydride that is used in the fuel.

18 Claims, No Drawings

RECYCLE OF DISCHARGED SODIUM BORATE FUEL

FIELD OF THE INVENTION

The present invention relates to processes for enhancing the recovery of boron values from alkali metal borates.

BACKGROUND OF THE INVENTION

Environmentally friendly fuels, e.g., alternatives to hydrocarbon based energy sources, are currently of great interest. Borohydride salts are an example of compounds which can be used directly as an anodic fuel in a fuel cell or as a hydrogen storage medium to enable hydrogen fuel cell applications. As a hydrogen storage material, alkali metal borohydrides produce hydrogen by a hydrolysis reaction, which also produces alkali metal borate salts as a byproduct. Further, when aqueous solutions of borohydride compounds are used as the hydrogen storage medium, it is preferable to add an alkaline stabilizing agent, typically an alkali metal hydroxide compound, to the mixture. This stabilizing agent is present unchanged in the discharged borate solution. In addition to the need to manufacture borohydride compounds in an energy efficient manner, there is a corresponding need to dispose of the large quantities of alkali metal borate salts that would result from extensive use of a borohydride-based fuel system, particularly given the quantities thereof that would be consumed, e.g. by the transportation industry. It will be appreciated that a particularly advantageous means of disposing of the alkali metal borates would be via a process that converts them back into borohydride compounds.

Processes are known whereby borate salts can be converted into trialkyl borates, which are the precursors in the current commercial process for the synthesis of borohydride. Preferred among these is the formation of trialkyl borate compounds which involves two steps. The first step is the acidification of the borate compound, e.g. borax, with an acid, primarily a strong acid such as sulfuric acid, to form boric acid and the alkali metal sulfate, as shown in Equation (1) wherein the alkali metal is sodium:

$$Na_2B_4O_7 + H_2SO_4 + 5H_2O \rightarrow 4B(OH)_3 + Na_2SO_4 \quad (1)$$
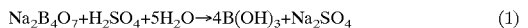

The second step is the reaction of the resultant boric acid with a lower alcohol to form the desired trialkyl borate as shown in Equation (2):

$$B(OH)_3 + 3ROH \rightarrow B(OR)_3 + 3H_2O \quad (2)$$

Wherein R is a saturated lower alkyl group

The trialkyl borate may then be converted to borohydride by a process shown in Equation (3), wherein Y is an alkali metal, preferably sodium.

$$B(OR)_3 + 4YH \rightarrow YBH_4 + 3\,YOR \quad (3)$$

The process of forming trialkyl borates from alkali metal borates, such as borax, by the reactions shown in Equations (1) and (2) is disadvantageous in three aspects. The first is the generation of large amounts of alkali metal sulfate, typically sodium sulfate that must be disposed of. Second, the fact that boric acid is formed in a separate step reduces the recovered boron value per pass as a result of limitations of the crystallization process. Finally, the water formed in the alcohol reaction shown in Equation (2), in combination with the desired trialkyl borate, can enter into an equilibrium with a reverse reaction back to boric acid which retards the reaction rate and, ultimately, can reduce the yield of the trialkyl borate.

Another method of obtaining trialkyl borates is by the direct acidification of alkali metal borate salts or borate ore with carbon dioxide in the presence of a lower alcohol at elevated temperatures as taught, for example, in Canadian Patent No. 624,125. This reaction, illustrated with methanol as the lower alcohol, is shown in Equation (4).

$$NaBO_2 + CO_2 + 3CH_3OH \rightarrow B(OCH_3)_3 + NaHCO_3 + H_2O \quad (4)$$
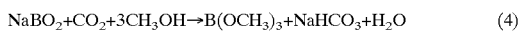

In this reaction, there is also an equilibrium in the reaction chamber between boric acid and trimethyl borate as discussed above. In this instance, both are recovered as products, boric acid by recognized crystallization techniques and trimethyl borate by distillation techniques. It is stated that the reaction is advantageously conducted in a grinding apparatus, such as a ball mill, to maintain the borate substrate material in a fine state of subdivision, thereby facilitating maximum contact among the reactants. It is also stated that the reaction is advantageously conducted at higher temperatures when the substrate borate material contains water of hydration since the higher temperature facilitates dehydration of the substrate. It is not stated how the water is removed from the reaction chamber other than the equilibrium reaction discussed above. In this instance, both the boric acid and trimethyl borate are recovered. Trimethyl borate yields of 16% are disclosed for sodium metaborate as a starting material at 500° C. and up to 67% for borax as a starting material at 600°C.

In U.S. Pat. No. 2,884,440, there is disclosed processes for the conversion of borax to trimethyl borate by the reaction with carbon dioxide and methanol at temperatures between 0° C. and 195° C. and pressures between 1 atm and 35 atm, which represents about 550 psig. The reaction is shown is Equation (5)

$$Na_2B_4O_7 \cdot xH_2O + CO_2 + nCH_3OH \rightarrow 4B(OCH_3)_3 + (x+6)H_2O + (n-12)CH_3OH + Na_2CO_3 \quad (5)$$
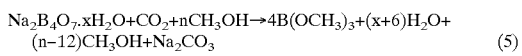

wherein x represents the number of moles of water of hydration of the sodium tetraborate (10 in the instance of borax) and n represents the number of moles of methanol added to the reaction mixture. It is disclosed that the sodium carbonate formed may, in turn, react with carbon dioxide and water present to form sodium bicarbonate. It is stated that both sodium carbonate and sodium bicarbonate can be calcined to recover carbon dioxide for use in the process.

The reactions shown in Equations (4) and (5) are important in that they demonstrate that the first step in the recovery of alkali metal borate can be carried out without the need to utilize a strong acid with the inherent danger of an uncontrolled hyperthermia that might result from a reaction with sodium hydroxide which is typically present in discharged fuel from a hydrogen generation apparatus. These reactions further demonstrate that, in producing trialkyl borates, there is significantly less difficulty in converting borax than sodium metaborate, which would be expected since borax is the more acidic of the two. However, these reactions are also limited by the accumulation of water in the reaction medium. Here also, the water tends to form an equilibrium with boric acid that will adversely affect both the rate of reaction and the yield of trialkyl borate as discussed above.

In view of the large volume of use contemplated for borohydride as a fuel, e.g., in the transportation industry, there is clearly a need for a process of recovering borohydride for future use that is cost-effective and environmentally acceptable. In order to meet these criteria, the process should readily separate boron from any sodium species present, avoid the use of strong acid and thereby prevent the danger of runaway hyperthermia, provide a boron species that is directly reducible to a boron hydride, and recover boron values in a cost-effective manner. It is further important that the process be carried out directly on the discharged fuel without the need to first separate the boron from the alkali metal hydroxide stabilizer. Such a process is provided in accordance with the present invention.

SUMMARY OF THE INVENTION

In accordance with the present invention, a process is provided for recovering boron value from a mixture of alkali metal hydroxide and alkali metal borate that represents the discharged fuel from a hydrogen generation apparatus. The process comprises initially dehydrating the discharged fuel solution, then treating it with carbon dioxide and a lower alcohol, preferably methanol, to form the corresponding trialkyl borate, alkali metal bicarbonate and water. The formation of the trialkyl borate is improved upon in accordance with the present invention by the presence of a solid, porous water-absorbing material in the reaction mixture to absorb water as it is formed, thus minimizing the formation of boric acid from the reaction of the trialkyl borate product and water. The trialkyl borate, preferably trimethyl borate, may be subsequently converted to a borohydride compound.

DESCRIPTION OF THE PREFERRED EMBODIMENTS

The discharged fuel from a hydrogen generation apparatus, such as used to supply a hydrogen fuel cell, is an aqueous solution of alkali metal hydroxide and alkali metal borate, typically a sodium borate represented by the formula $Na_2O \cdot xB_2O_3 \cdot yH_2O$, wherein x is 1 to 5 and y is 0 to 10. The alkali metal ion in both of these is typically sodium, although other alkali metal ions, such as potassium, may be utilized. The alkali metal hydroxide is a stabilizer in the fuel solution that does not enter into the reaction in either hydrogen generation or the subject process. Typically, the fuel solution that is introduced into a hydrogen fuel cell will be comprised of from about 20% to 35% by wt. sodium borohydride and from about 0.01 to 5% by weight sodium hydroxide as a stabilizer. The discharged fuel will contain sodium metaborate and sodium hydroxide in a corresponding molar concentration, but the percent by weight of sodium metaborate will be from about 36% to 66% by weight as a result of the higher molecular weight thereof in comparison to sodium borohydride, and the reduced amount of water present. The discharged fuel may be a solution, a heterogeneous mixture or a slurry depending on the concentration of the ingredients and the temperature. It is to be noted that the term "about", as used herein, means ±10% of the stated value.

In accordance with the present invention, the discharged fuel is initially dehydrated at a temperature of from about 30° to 100° C. under mild vacuum, i.e. from 0.001 to 5 psig for from about 4 to 48 hours. This process removes a substantial amount of the water from the discharged fuel resulting essentially in a mixture of sodium hydroxide and $NaBO_2 \cdot x\ H_2O$ wherein x is 0.5 to 3, using sodium as the alkali metal. This mixture is charged to a batch reactor where it is combined with a lower alcohol. Alcohols suitable for the process of the present invention include straight- or branched-chain alkyl alcohols containing from 1 to 6, preferably from 1 to 4, carbon atoms. To be useful in the subject process, the alcohol must be a solvent for the alkali metal borate and form a trialkyl borate that can readily be isolated from the reaction mixture by distillation. Preferred alcohols are methanol and n-butanol.

The amount of lower alcohol added to the reaction vessel may vary within a considerable range. However, for practical considerations, an amount is added which is from one to about 5 times the stoichiometric amount that would react with all of the alkali metal borate present in the charge. It is not necessary to have a large excess of lower alcohol present. This is preferred because the excess is recovered for recycle into the process. The reactor is then pressurized with carbon dioxide to a pressure of from about 1 atm. to 35 atm. (550 psig), preferably from about 15 atm. to 35 atm., for from about 1 to 10 hours, which converts the alkali metal hydroxide into alkali metal bicarbonate and the alkali metal borate into trialkyl borate and alkali metal bicarbonate. The product trialkyl borate is isolated from the reaction by distillation. The excess lower alcohol and the sodium bicarbonate formed therein are recovered and recycled into the process and/or the steps subsequently carried out to regenerate the borohydride fuel material, for example, as described in U.S. Pat. No. 6,433,129 and U.S. Pat. No. 6,524,542. The reactions in the reactor are as according to Equation (6a) and (6b) reproduced below, using sodium as the alkali metal:

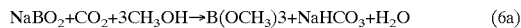
$$NaBO_2 + CO_2 + 3CH_3OH \rightarrow B(OCH_3)_3 + NaHCO_3 + H_2O \quad (6a)$$

$$NaOH + CO_2 \rightarrow NaHCO_3 \quad (6b)$$

The overall reaction is according to Equation 6(c) in which it can be seen that both the sodium borate and sodium hydroxide are thus converted to methyl borate and sodium bicarbonate.

$$NaBO_2 + NaOH + 2CO_2 + 3CH_3OH \rightarrow B(OCH_3)_3 + 2NaHCO_3 + H_2O \quad (6c)$$

The reaction may also be carried out in a continuous manner. In this embodiment, the reactor is equipped such that gas may flow therethrough. The mixture from the discharged fuel is admitted to the reactor and carbon dioxide and either liquid or gaseous lower alcohol is made to flow thereover in the reactor under the same conditions of temperature and pressure as stated above with regard to the batch method. The resultant trialkyl borate, sodium bicarbonate and the excess lower alcohol are recovered as described above. Carbon dioxide is recovered from the gas effluent of the reactor for recycle into the process. The means whereby these materials are recovered are well known to one of ordinary skill in the art. The recovered sodium bicarbonate can be heated to convert it to sodium carbonate for use in a subsequent synthesis steps as described in U.S. Pat. No. 6,524,542 to give sodium borohydride. While the process will be described herein with regard to the formation of trialkyl borate, it should be borne in mind that, if the desired product is boric acid, it can be formed from the trialkyl borate in virtually quantitative yield simply by combining it with water.

As noted above, trialkyl borate will react quantitatively with water to form boric acid. In a reaction vessel as described above, whether the reaction is a batch in a closed vessel or a continuous one where gaseous carbon dioxide and a lower alcohol are made to flow over a borate substrate, an equilibrium will take place between boric acid and the lower alcohol on one side and the product trialkyl borate and water on the other, as shown in Equation (7).

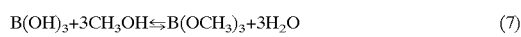
$$B(OH)_3 + 3CH_3OH \rightleftharpoons B(OCH_3)_3 + 3H_2O \quad (7)$$

It will be appreciated that, unless this equilibrium is driven to favor the formation of the trialkyl borate as much as possible, the yield thereof will be adversely affected. Previously, this was accomplished by distilling trialkyl borate from the system as it was formed. This has not been totally effective in view of the volatile nature of the reactants in the system, as well as the small differential in boiling points. It will be appreciated that it is advantageous to have excess lower alcohol in the reactor since the excess would aid in driving the equilibrium shown in Equation (7) toward the formation of the trialkyl borate product. The removal of water becomes more difficult in a continuous or flow-through system where a gaseous stream is continuously being withdrawn from the reactor.

The aforementioned difficulties in removing water from the reaction vessel are overcome in accordance with the present invention by the inclusion in the reaction vessel of solid phase, porous, water-absorbing material. Such agents are well known and are commercially available. Suitable materials include alumina pellets and molecular sieves of Type 3A and 4A (respective pore sizes of 3Å and 4Å in diameter) that are selective for water. While the water-adsorbing material may be present as a large mass within the reactor, it is preferred that it be in particulate form, thereby exposing more surface for the absorption of water. While the specific particle size of the water-absorbing material is not particularly critical, in general, it should have a particle size at least about equal to the particle size of the substrate for the reaction. A preferred particle size range is between about 0.1 and 5 mm.

It has been found in accordance with the present invention that inclusion of a porous water-absorbing solid material in the reaction vessel for the reaction of an alkali metal borate with carbon dioxide and a lower alcohol to produce a trialkyl borate will increase the yield relative to the absence of such a material by close to fifty percent, a significant increase. Such water-absorbing materials are added to the reactor in excess of an amount that would be required to absorb the calculated amount of water formed in the reaction. In a batch reaction, such amounts can be readily calculated by determining the moles of water that will result from a known quantity of borate starting material and then determining the amount of absorbing material required based on its capacity to absorb water. At the conclusion of the reaction, the material is recovered and discarded, or preferably regenerated for recycle by heating to remove the absorbed water.

Wherein the reaction forming trialkyl borates is conducted in a continuous flow reactor as described above, it is again possible, based on the dynamics of the reaction, to determine the amount of water being formed on a continuous basis and provide the required quantity of water-absorbing material in the reactor. Thereafter, the water-absorbing material can be replaced or added at the same time and relative rate as the particulate substrate material.

The improvement in the formation of trialkyl borates afforded by the present invention is advantageous in that it also represents an improvement in the overall process of regenerating the borohydride material that is utilized as fuel in hydrogen generators. In the current commercial process, trimethyl borate is reacted with four equivalents of sodium hydride to form one equivalent of sodium borohydride and three equivalents of sodium methoxide. This reaction is shown in equation (8):

$$B(OCH_3)_3 + 4NaH \rightarrow NaBH_4 + 3NaOCH_3 \qquad (8)$$

The following examples further illustrate the invention, it being understood that the invention is in no way intended to be limited by the details disclosed therein.

EXAMPLE 1

A sealed glass reactor was charged with 2.0 g of sodium metaborate and either 15 g of methanol or 35 g of n-butanol as shown below. The reactor contained a water-absorbing material comprising either 2.0 g of a molecular sieve (3A or 4A, available from Aldrich, Inc.) or 2.0 g of porous alumina having a particle size of 3.2 mm available from Alfa Aesar, Inc. The reactor was filled with carbon dioxide and held at 80° C. for four hours. The resulting trialkyl borate and residual alcohol were removed by distillation from the reactor. A control reaction was run without including either the molecular sieve or alumina The results are shown in the following Table.

| Alcohol | Temperature (° C.) | Pressure (psig) | Water-absorbing material | Yield of Trialkyl Borate |
|---|---|---|---|---|
| Methanol | 80 | 20 | none | 28% |
| Methanol | 80 | 20 | Molecular Sieve | 38% |
| Methanol | 80 | 20 | Alumina | 43% |
| n-Butanol | 80 | 20 | Alumina | 38% |

It can be seen from the results in the Table that the addition of a water-absorbing material produces a significant increase, about 50%, in the production of the desired trialkyl borate.

What is claimed is:

1. A process for producing trialkyl borates of the formula $B(OR)_3$, wherein R is a straight- or branched-alkyl consisting of 1 to 6 carbon atoms, comprising reacting an alkali metal borate with carbon dioxide and a lower alcohol thereby producing trialkyl borate, alkali metal bicarbonate and water, said reaction being carried out in the presence of a porous particulate water-absorbing material to absorb said water as it forms.

2. The process in accordance with claim 1, wherein the alkali metal borate is a sodium borate represented by the formula $Na_2O \cdot xB_2O_3 \cdot yH_2O$, wherein x is 1 to 5 and y is 0 to 10, and the lower alcohol is a straight- or branched-chain alkyl alcohol containing from 1 to 6 carbon atoms.

3. The process in accordance with claim 2, wherein said lower alcohol is a straight- or branched-chain alkyl alcohol containing from 1 to 4 carbon atoms.

4. The process in accordance with claim 3, wherein the lower alcohol is methanol or n-butanol.

5. The process in accordance with claim 1, wherein said water-absorbing material is a molecular sieve of Type 3A or 4A, or particulate alumina.

6. The process in accordance with claim 1, wherein said reaction is carried out in a continuous manner by passing the carbon dioxide and lower alcohol over a particulate mixture of alkali metal borate and said water-absorbing material.

7. The process in accordance with claim 1, wherein the trialkyl borate is isolated by distillation.

8. A process for producing trialkyl borates of the formula $B(OR)_3$, wherein R is a straight- or branched-alkyl consisting of 1 to 6 carbon atoms, from a solution of alkali metal borate and alkali metal hydroxide comprising:

a. drying said solution to form a particulate mixture of alkali metal borate and alkali metal hydroxide; and b. reacting said particulate mixture with carbon dioxide and a lower alcohol thereby producing trialkyl borate, alkali metal bicarbonate and water, said reaction being carried out in the presence of a porous particulate water-absorbing material to absorb water as it forms.

9. The process in accordance with claim 8, wherein the alkali metal borate is a sodium borate represented by the formula $Na_2O \cdot xB_2O_3 \cdot yH_2O$, wherein x is 1 to 5 and y is 0 to 10, the alkali metal hydroxide is sodium hydroxide, and the lower alcohol is a straight- or branched-chain alkyl alcohol containing from 1 to 6 carbons.

10. The process in accordance with claim 9, wherein said lower alcohol is a straight-or branched-chain alkyl alcohol containing from 1 to 4 carbon atoms.

11. The process in accordance with claim 10, wherein the lower alcohol is methanol or n-butanol.

12. The process in accordance with claim 8, wherein said reaction is carried out in a continuous manner by passing the carbon dioxide and lower alcohol over the particulate mixture of alkali metal borate and alkali metal borohydride and said water-absorbing material.

13. The process in accordance with claim 8, wherein said water-absorbing material is a molecular sieve of Type 3A or 4A, or particulate alumina.

14. The process in accordance with claim 8, wherein the trialkyl borate is isolated by distillation.

15. The process in accordance with claim 8, wherein the unreacted lower alcohol is recovered and reused in the process.

16. The process in accordance with claim 8, wherein the solution containing alkali metal borate and alkali metal hydroxide is discharged fuel from a hydrogen generator.

17. The process in accordance with claim 8, additionally including the step of converting the trialkyl borate to an alkali metal borohydride by reaction with an alkali metal hydride.

18. The process in accordance with claim 17, wherein the alkali metal is sodium.

* * * * *

UNITED STATES PATENT AND TRADEMARK OFFICE
CERTIFICATE OF CORRECTION

PATENT NO. : 6,706,909 B1
DATED : March 16, 2004
INVENTOR(S) : Jonathan Snover et al.

It is certified that error appears in the above-identified patent and that said Letters Patent is hereby corrected as shown below:

Column 7,
Line 18, please change "borohydride" to read -- hydroxide --.

Signed and Sealed this

Fourteenth Day of December, 2004

JON W. DUDAS
*Director of the United States Patent and Trademark Office*